United States Patent
Taulu et al.

(10) Patent No.: US 11,540,778 B2
(45) Date of Patent: Jan. 3, 2023

(54) REDUCING SENSOR NOISE IN MULTICHANNEL ARRAYS USING OVERSAMPLED TEMPORAL PROJECTION AND ASSOCIATED SYSTEMS AND METHODS

(71) Applicant: University of Washington, Seattle, WA (US)

(72) Inventors: Samu Taulu, Seattle, WA (US); Eric D. Larson, Seattle, WA (US)

(73) Assignee: University of Washington, Seattle, WA (US)

( * ) Notice: Subject to any disclaimer, the term of this patent is extended or adjusted under 35 U.S.C. 154(b) by 1046 days.

(21) Appl. No.: 16/095,663

(22) PCT Filed: May 26, 2017

(86) PCT No.: PCT/US2017/034667
§ 371 (c)(1),
(2) Date: Oct. 22, 2018

(87) PCT Pub. No.: WO2017/205734
PCT Pub. Date: Nov. 30, 2017

(65) Prior Publication Data
US 2019/0125268 A1    May 2, 2019

Related U.S. Application Data

(60) Provisional application No. 62/342,109, filed on May 26, 2016.

(51) Int. Cl.
*A61B 5/245*    (2021.01)
*A61B 5/00*    (2006.01)
(Continued)

(52) U.S. Cl.
CPC ............ *A61B 5/7203* (2013.01); *A61B 5/245* (2021.01); *A61B 5/318* (2021.01); *A61B 5/352* (2021.01);
(Continued)

(58) Field of Classification Search
None
See application file for complete search history.

(56) References Cited

U.S. PATENT DOCUMENTS 7,696,748 B2    4/2010    Schlicker et al.
7,933,727 B2    4/2011    Taulu et al.
(Continued)

FOREIGN PATENT DOCUMENTS

| EP | 2806789 A1 | 1/2013 |
|----|------------|--------|
| WO | 2013111072 A1 | 8/2013 |
| WO | 2015047462 A2 | 4/2015 |

OTHER PUBLICATIONS

International Search Report and Written Opinion dated Aug. 10, 2017 in International Patent Application No. PCT/US2017/034667, 12 pages.

(Continued)

*Primary Examiner* — Ankit D Tejani
(74) *Attorney, Agent, or Firm* — Perkins Coie LLP

(57) ABSTRACT

A method for suppressing sensor noise in a spatially oversampled sensor array includes receiving spatially oversampled multi-channel sensor data from a region of interest and building a spatial model from the data for essential spatial degrees of freedom. The method further includes decomposing the data into the underlying spatial model to obtain associated amplitude components containing a mixture of original temporal waveforms of the data and, for each channel of the multi-channel sensor, estimating time-domain amplitude components using cross-validation. Next, for (Continued)

each channel, based on the estimated time-domain amplitude components, sensor noise and/or artifacts for that channel are identified. Finally, for each channel, the identified sensor noise and/or artifacts can be suppressed from the data.

5 Claims, 7 Drawing Sheets

(51) Int. Cl.
  *A61B 5/318*  (2021.01)
  *A61B 5/352*  (2021.01)
  *A61B 5/369*  (2021.01)
  *G06K 9/00*  (2022.01)

(52) U.S. Cl.
  CPC .......... *A61B 5/369* (2021.01); *G06K 9/00516* (2013.01)

(56) References Cited

U.S. PATENT DOCUMENTS

| | | |
|---|---|---|
| 9,008,399 B2 | 4/2015 | Fain et al. |
| 2008/0161714 A1 | 7/2008 | Ahonen et al. |
| 2008/0294386 A1 | 11/2008 | Taulu et al. |
| 2009/0069661 A1 | 3/2009 | Taulu et al. |
| 2009/0184709 A1 | 7/2009 | Kajola et al. |
| 2013/0109954 A1 | 5/2013 | Simola et al. |
| 2014/0343882 A1 | 11/2014 | Taulu et al. |
| 2016/0051163 A1 | 2/2016 | Deouell et al. |
| 2016/0113587 A1 | 4/2016 | Kothe et al. |

OTHER PUBLICATIONS

Ahonen, A. et al., "Sampling theory for neuromagnetic detector arrays." IEEE Transactions on Biomedical Engineering, 40(9):859-869, Sep. 1993.
Arnold, M. et al., "Adaptive AR modeling of nonstationary time series by means of Kalman filtering," IEEE Transactions on Biomedical Engineering, vol. 45, No. 5, pp. 553-562, May 1998.
Bartoli, F. et al., "An optimal linear filter for the reduction of noise superimposed to the EEG signal," Journal of Biomedical Engineering, vol. 5, No. 4, pp. 274-280, Oct. 1983.
Chella, F., et al., "Calibration of a multichannel MEG system based on the Signal Space Separation method," Physics in Medicine & Biology, 57, 17 pages.
Dale, A. et al., "Cortical surfacebased analysis." I. Segmentation and surface Yeconstruction. Neuroimage, 9:179-194, 1999.
Dale, A. et al., "Dynamic statistical parametric mapping: combining fMRI and MEG for high-resolution imaging of cortical activity." Neuron, 26(1):55-67, Mar. 2000.
De Cheveign, A. et al., "Denoising based on time-shift PCA," Journal of Neuroscience Methods, vol. 165, No. 2, pp. 297-305, Sep. 2007.
De Cheveigne, A. et al., "Denoising based on spatial filtering," Journal of Neuroscience Methods, vol. 171, Issue 2, pp. 331-339.
De Cheveigne, A. et al., "Sensor noise suppression," Journal of Neuroscience Methods, vol. 168, No. 1, pp. 195-202, Feb. 2008.
De Cheveigne, A., "Sparse time artifact removal," Journal of Neuroscience Methods, vol. 262, pp. 14-20, Mar. 2016.
Fries, P. et al., "Finding Gamma," Neuron, vol. 58, No. 3, pp. 303-305, May 2008.
Gramfort, A. et al., "MEG and EEG data analysis with MNE-Python," Frontiers in Brain Imaging Methods, vol. 7, p. 267, 2013.
Gramfort, A. et al., "MNE software for processing MEG and EEG data." NeuroImage, 86: 446-460, Feb. 2014.
Hamalainen, M. et al., "Interpreting magnetic fields of the brain: minimum norm estimates," Medical & Biological Engineering & Computing, vol. 32, No. 1, pp. 35-42, Jan. 1994.

Hamalainen, R. et al., "Magnetoencephalography—theory, instrumentation, and applications to noninvasive studies of the working human brain." Reviews of modern Physics, 65 (2):413-497, 1993.
Helle, L. et al., "Suppression of uncorrelated sensor noise and artifacts: Demonstration with high frequency brain signals." Presented at the 18th International Conference on Biomagnetism, Paris, France, 2012.
Hunter, J. et al., "Matplotlib: A 2d graphics environment." Computing In Science & Engineering, 9(3):90-95, 2007.
Johnson, C. et al., "Multi-sensor magnetoencephalography with atomic magnetometers," Physics in Medicine & Biology, 58, 14 pages.
Korber, R. et al., "SQUIDs in biomagnetism: a roadmap towards improved healthcare," 2016 Superconductor Science and Technology, 29, 31 pages.
Kupers, E., "Broadband spectral responses in visual cortex revealed by a new MEG denoising algorithm," bioRxiv, p. 108993, Feb. 2017. [Online], Available: http://biorxiv.org/content/early/2017/02/16/108993.
Lesur, V. "Introducing localized constraints in global geomagnetic field modelling," Earth, Planets and Space, vol. 58, No. 4, pp. 477-483, Apr. 2006.
Miller, K. et al., "Broadband changes in the cortical surface potential track activation of functionally diverse neuronal populations," NeuroImage, vol. 85, Part 2, pp. 711-720, Jan. 2014.
Mosher, J., et al., "EEG and MEG: forward solutions for inverse methods." Biomedical Engineering, IEEE Transactions on, 46(3):245-259, 1999.
Nenonen, J. et al., "Magnetocardiographic functional localization using a current dipole in a realistic torso," IEEE Transactions on Biomedical Engineering, vol. 38, No. 7, pp. 658-664, Jul. 1991.
Nenonen, J. et al., "Noninvasive Functional Localization by Biomagnetic Methods: Part I." Journal of Clinical Engineering, vol. 16, No. 5, 1991.
Niedermeyer, E., "Electroencephalography: Basic Principles, Clinical Applications and Related Fields," 5th ed. Philadelphia: Lippincott Williams and Wilkins, Nov. 2004. Book will be mailed to USPTO.
Nurminen, J et al., "Effects of sensor calibration, balancing and parametrization on the SSS method," Physics in Medicine and Biology, May 2008, 14 pages.
Nurminen, J. et al., "Improving the performance of the SSS method by comprehensive spatial sampling," Physics in Medicine & Biology, 55, 14 pages.
Okada, Y. et al., "BabySQUID: A mobile, highresolution multichannel magnetoencephalography system for neonatal brain assessment," Review of Scientific Instruments, vol. 77, No. 2, p. 024301, Feb. 2006.
Ryhanen, T. et al., "SQUID magnetometers for low-frequency applications," Journal of Low Temperature Physics, vol. 76, No. 5-6, pp. 287-386, Sep. 1989.
Sabaka, T. et al., "Extending comprehensive models of the Earth's magnetic field with rsted and CHAMP data," Geophysical Journal International, vol. 159, No. 2, pp. 521-547, Nov. 2004.
Sarvas, J., "Basic mathematical and electromagnetic concepts of the biomagnetic inverse problem," Physics in Medicine and Biology, vol. 32, No. 1, p. 11, 1987.
Sekihara, K. et al., "Dual signal subspace projection (DSSP): a novel algorithm for removing large interference in biomagnetic measurements," J Neural Eng. Jun. 2016, 43 pages.
Tadel, F. et al., "Brainstorm: A User-Friendly Application for MEG/EEG Analysis," Computational Intelligence and Neuroscience, vol. 2011, p. e879716, Apr. 2011.
Tank, S. "Rotation of the geomagnetic field about an optimum pole," Geophysical Journal International, vol. 140, No. 2, pp. 461-464, Feb. 2000.
Taulu S., et al. "Suppression of uncorrelated sensor noise and artifacts in multichannel MEG data." Abstracts of the 18th international conference on biomagnetism, Paris 2012, p. 285.
Taulu, S. et al., "Suppression of interference and artifacts by the Signal Space Separation Method." Brain Topography, 16(4):269-275, 2004.

(56) References Cited

OTHER PUBLICATIONS

Taulu, S. et al., "Presentation of electromagnetic multichannel data: The signal space separation method," Journal of Applied Physics, vol. 97, No. 12, p. 124 905-124 905-10, Jun. 2005.

Taulu, Samu et al., "Spatiotemporal signal space separation method for rejecting nearby interference in MEG measurements.", Physics in medicine and biology 51.7 (2006): 1759.

Uno, Y. et al., "Development of a generative model of magnetoencephalography noise that enables brain signal extraction from single-epoch data," Medical & Biological Engineering & Computing, vol. 51, No. 8, pp. 937-951, May 2013.

Uusitalo, M. et al., "Signal-space projection method for separating MEG or EEG into components," Medical & Biological Engineering & Computing, vol. 35, No. 2, pp. 135-140, Mar. 1997.

Van der Walt, S. et al., "The NumPy Array: A Structure for Efficient Numerical Computation." Computing in Science & Engineering, 13(2):22-30, Mar. 2011.

Van Klink, N., et al., "Identification of epileptic high frequency oscillations in the time domain by using MEG beamformer-based virtual sensors," Clinical Neurophysiology, vol. 127, No. 1, pp. 197-208, Jan. 2016.

Vrba, J. et al., "Biomagnetism," in The SQUID Handbook, J. Clarke and A. I. Braginski, Eds. Wiley-VCH Verlag GmbH & Co. KGaA, 2006, pp. 269-389.

Walt, S. et al., "The NumPy Array: A Structure for Efficient Numerical Computation," Computing in Science & Engineering, vol. 13, No. 2, pp. 22-30, Mar. 2011.

Wood, C. "Application of Dipole Localization Methods to Source Identification of Human Evoked Potentials*," Annals of the New York Academy of Sciences, vol. 388, No. 1, pp. 139-155, Jun. 1982.

Zijlmans, M. et al., "High-frequency oscillations mirror disease activity in patients with epilepsy," Neurology, vol. 72, No. 11, pp. 979-986, Mar. 2009.

De Cheveigne, Alaine et al., "Sensor noise suppression.", Journal of neuroscience methods 168.1 (2008): 195-202.

REDUCING SENSOR NOISE IN MULTICHANNEL ARRAYS USING OVERSAMPLED TEMPORAL PROJECTION AND ASSOCIATED SYSTEMS AND METHODS

This application claims the benefit of U.S. Provisional Application No. 62/342,109, filed May 26, 2016, which is incorporated by reference herein in its entirety.

BACKGROUND

Technical Field

The present application generally relates to reducing sensor noise in multichannel measurement techniques including, for example, magnetoencephalography (MEG) and electroencephalography (EEG).

Background

Multichannel measurement techniques are typically used to record signals emitted by some object of interest in order to obtain data on spatial or temporal structures of the object. The object may be, e.g., the human brain with electric currents flowing in the brain tissue, reflecting ongoing resting-state activity or responses to external stimuli. The corresponding multichannel measurement could be related either to the detection of the magnetic fields or electric potential outside the head. These measurement techniques are called magnetoencephalography (MEG) and electroencephalography (EEG), respectively. Other measurements of magnetic fields include, for example, geomagnetic measurements with the aim of revealing information about the electric fluctuations taking place under the surface of the earth, and magnetocardiography (MCG) recordings of the magnetic fields produced by the heart. In general, embodiments of the present technology can be applied to any measurement that provides oversampling of the signal of interest with a multitude of sensors whose intrinsic sensor noise and artifacts can be considered statistically independent between channels and also with the actual signal of interest.

As a prerequisite for the analysis of a multichannel measurement, the acquired signals must usually be processed against environmental interference, and sometimes certain signals generated by the object itself with temporal or spatial structures that mask the actual target of the analysis must be suppressed as well. The spatial processing methods act as spatial filters that suppress certain spatial patterns by forming suitable linear combinations of all or of a subset of channels. Temporal processing methods alter the data in the temporal domain by, e.g., decomposing the signals into Fourier components and reconstructing the modified signals from a subset of frequency components so as to suppress signals from frequency bands that are not of interest in the analysis. In both of the above approaches, one exploits some a priori information about the spatial or temporal distribution of the signal of interest, and, if available, differences of these distributions in relation to signal components that are considered interference.

The intrinsic sensor noise, however, may also compromise the analysis results. Efficient suppression against this kind of noise is difficult because typically only some statistical information is available about its temporal and spatial structure. There is literature available on the hardware mechanisms causing device-related noise, but this information usually does not help to construct exact mathematical models for sample-by-sample suppression of the noise. In MEG, for example, researchers often know the levels of the standard deviation of intrinsic noise at different channels, but the noise fluctuations are random processes without a deterministic temporal or spatial pattern and, therefore, they are mixed between channels in the spatial filtering or have residual in the pass-band during temporal filtering. The aforementioned mixing that arises in spatial filtering is important because the spatial models do not have an accurate representation for the random sensor noise. Therefore, for any given moment of time, the momentary spatial distribution of the sensor noise values gets redistributed among measurement channels through a spatial model, which requires accurate a priori information about the spatial signal structures. This may be especially harmful if a specific artifact with temporal pattern resembling a potential signal of interest, but appearing in one channel only, spreads among other channels and may thus appear as a signal of interest, both spatially and temporally. Traditionally, the only reliable procedure to avoid such channel artifact spreading is visual inspection of the original data and manual rejection of bad channels or segments of time in signal processing and analysis. With modern MEG systems containing hundreds of channels, visual inspection of raw data is cumbersome and may significantly hamper clinical work, which is time-sensitive in nature. Accordingly, automated sensor noise suppression is desirable.

Suppression of sensor noise is most beneficial in the analysis of weak signal components of interest that correspond to a frequency band initially dominated by uncorrelated sensor noise. An example of such signals in biomagnetic measurements is the high-frequency oscillations (HFO) related to epilepsy. HFO signals are hypothesized to contain significant clinical value but their detection with MEG or EEG is difficult. Broadband forms of high-frequency activity, e.g., over 60 Hz, which are often observed in intracranial recordings, are also difficult to isolate using MEG or EEG. On the other hand, high frequencies are usually not significantly contaminated by external interference signals, so the main component compromising the signal-to-noise ratio is random sensor noise. Thus, sensor noise suppression could play a major role in improving the detectability of HFO and broadband signals in EEG and MEG.

MEG and EEG are commonly used to detect brain responses to events such as auditory, visual, or somatosensory stimuli. Even in favorable measurement conditions, individual responses are often too weak to be detected under sensor noise. Therefore, several repetitions of the evoked responses are collected and averaged in order to suppress the contribution of noise that is independent of the stimulus presentation. In such a case, the signal-to-noise ratio improves proportionally to $\sqrt{N_t}$, where $N_t$ is the number of trials. With a lower initial sensor noise level, a satisfactory signal-to-noise ratio could be reached with a smaller $N_t$, which would enable shorter measurements and reduce the effects of habituation in the analysis assuming accurate repeatability of the evoked response.

DETAILED DESCRIPTION

Figure 1:
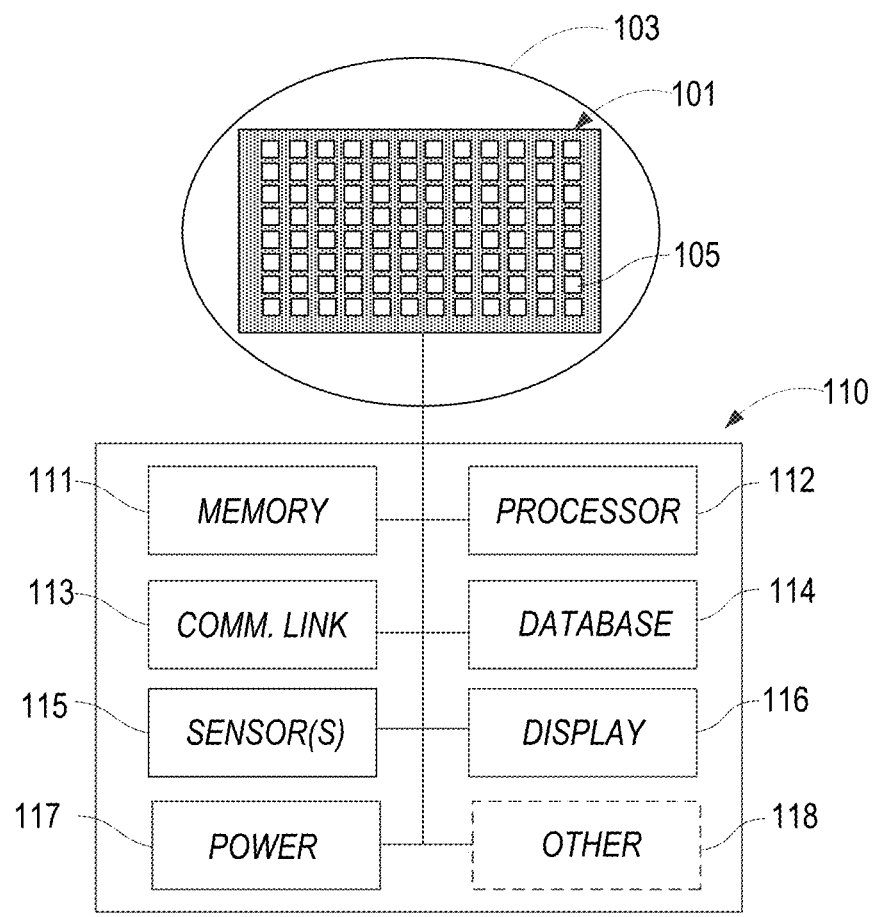
FIG. 1 is a schematic diagram of a multi-channel sensor system configured in accordance with embodiments of the present technology.

The present technology is generally related to methods for sensor noise and artifact suppression that do not require user intervention or assumptions about the spatial and temporal structures of the noise, other than statistical independence between the noise and signals of interest and spatial oversampling of the signals of interest. Spatial oversampling is a reasonable assumption for MEG and EEG data, but applies equally well in many other potential domains. The disclosed techniques, referred to herein as "oversampled temporal projection" (OTP), operate on overlapping windowed segments of data. Within each window, each channel is projected onto the temporal basis formed by all other channels, and the residual is taken as an estimate of the sensor noise signal of the channel that can be suppressed for efficient sensor noise suppression. As described below, this procedure can be automatically performed on each channel at a time without any user intervention. This method is expected to minimize spreading of channel artifacts to other channels, a feature that may be of particular relevance in clinical work. In addition to facilitating signal analysis workflows by reducing the burden of visual data inspection with respect to sensor artifacts, the disclosed technique is expected to make signal processing and analysis of multichannel data more robust. OTP can be used as a first step in a chain of signal processing procedures, as any other spatial filters used in signal processing or analysis will have significantly reduced spreading of channel artifacts when the signals have first been processed with OTP.

State-of-the-Art Noise Suppression Techniques

To address problems caused by sensor noise, multiple algorithms have been developed. Some of the most relevant state-of-the art sensor noise suppression methods include a method developed primarily for EEG that uses Kalman filtering targeted to remove electromyography (EMG) artifacts, but requires making a priori assumptions about the nature of noise—in particular that it consists of spikes with a Poisson distribution—which make this method less well suited in general for reducing sensor noise. Adaptive autoregressive (AR) modeling of noise has also been proposed, but requires an assumption of time dependence of samples and Gaussian distribution of noise sources. More recently, a temporal artifact removal method was developed specifically for MEG, but assumes a parametric generative model for MEG data, which might not generalize to all forms of sensor-specific noise and artifacts.

Cross-validation (CV) based algorithms have recently been developed to address sensor noise. In CV methods, one channel at a time is left out from the acquired data and the associated data models, and the signal of the channel under investigation is then reconstructed based on all other channels or a suitable subset of channels. More formally, the procedure assumes spatial oversampling of the signal of interest and a spatial model that only contains the essential spatial features capable of explaining the data. Thus, the measured signals can be projected onto the parameters of the model and these parameters can subsequently be used to reconstruct the signal of the channel that was left out. It is evident that in such a procedure the individual noise of the channel that was left out will be absent in the reconstructed signal, but the challenge remains that part of the noise on the other channels will distort the reconstructed signal. The "sensor noise suppression" (SNS) algorithm, which uses the correlation between channels to build a spatial denoising operator, is one example of such a CV algorithm. More recently, another CV-based algorithm utilizing vector spherical harmonics as the spatial basis was introduced.

Denoising algorithms can also be performed in multiple (time) segments, which has been suggested as one way to overcome computational challenges. However, such window-based processing can effectively change the process from linear time invariant to linear time varying. Window-based processing could thus also provide potential benefits in terms of denoising quality, especially in cases where the set of sensors operating optimally changes gradually over time. A variant of this time-varying processing idea is utilized by the sparse-time artifact removal (STAR) algorithm, which uses statistical thresholding to identify temporally sparse artifacts and subsequently repair them individually with a SNS-like operation.

Suitable System(s)

The following discussion provides a brief, general description of a suitable environment in which the present technology may be implemented. Although not required, aspects of the technology are described in the general context of computer-executable instructions, such as routines executed by a general-purpose computer. Aspects of the technology can be embodied in a special purpose computer or data processor that is specifically programmed, configured, or constructed to perform one or more of the computer-executable instructions explained in detail herein. Aspects of the technology can also be practiced in distributed computing environments where tasks or modules are performed by remote processing devices, which are linked through a communication network (e.g., a wireless communication network, a wired communication network, a cellular communication network, the Internet, a short-range radio network (e.g., via Bluetooth)). In a distributed computing environment, program modules may be located in both local and remote memory storage devices.

Computer-implemented instructions, data structures, screen displays, and other data under aspects of the technology may be stored or distributed on computer-readable storage media, including magnetically or optically readable computer disks, as microcode on semiconductor memory, nanotechnology memory, organic or optical memory, or other portable and/or non-transitory data storage media. In some embodiments, aspects of the technology may be distributed over the Internet or over other networks (e.g. a Bluetooth network) on a propagated signal on a propagation medium (e.g., an electromagnetic wave(s), a sound wave) over a period of time, or may be provided on any analog or digital network (packet switched, circuit switched, or other scheme).

FIG. 1 is a schematic diagram of a system 100 configured in accordance with an embodiment of the disclosed technology. The system 100 includes a multi-channel sensor module 101 disposed over a region of interest 103. The multi-channel sensor module 101 can include a plurality of individual sensors 105. The multi-channel sensor module 101 can be any type of sensor, for example, a MEG sensor array, an EEG sensor array, geomagnetic sensor array, magnetocardiography (MCG) sensor array, etc. The region of interest 103 can be, for example, a patient's head in the case of EEG or MEG sensors, a region of earth in the case of geomagnetic sensors, or a patient's heart in the case of MCG sensors. It will also be appreciated that the region of interest 103 may comprise other suitable anatomical and/or geographic locations.

The multi-channel sensor module 101 can be configured such that the combination of individual sensors 105 provides spatial oversampling of the signal of interest (i.e., the multi-channel sensor module 101 contains more individual sensors 105 or measurement channels than degrees of freedom in the detectable signal with a spatially correlated structure). The multi-channel sensor module 101 can be communicatively coupled to a processing subsystem 110 as described in more detail below.

The processing subsystem 110 comprises several components including memory 111 (e.g., one or more computer readable storage modules, components, devices) and one or more processors 112. The memory 111 can be configured to store information (e.g., signal data, subject information or profiles, environmental data, data collected from one or more sensors, media files) and/or executable instructions that can be executed by the one or more processors 112. The memory 111 can include, for example, instructions for processing multi-channel sensor data and suppressing noise and other artifacts from individual channels.

The processing subsystem 110 also includes communication components 113 (e.g., a wired communication link and/or a wireless communication link (e.g., Bluetooth, Wi-Fi, infrared and/or another wireless radio transmission network)) and a database 114 configured to store data (e.g., signal data acquired from the region of interest, equations, filters) used in the noise-suppression techniques disclosed herein. One or more sensors 115 can provide additional data for use in noise-suppression and/or other signal processing and analysis. The one or more sensors 115 may include, for example, one or more ECG sensors, blood pressure monitors, galvanometers, accelerometers, thermometers, hygrometers, blood pressure sensors, altimeters, gyroscopes, magnetometers, proximity sensors, barometers and/or hall effect sensors. One or more displays 116 can provide video output and/or graphical representations of data obtained by the system 100. A power supply 117 (e.g., a power cable connected to a building power system, one or more batteries and/or capacitors) can provide electrical power to components of the processing subsystem 110 and/or the system 100. In embodiments that include one or more batteries, the power supply 117 can be configured to recharge, for example, via a power cable, inductive charging, and/or another suitable recharging method. Furthermore, in some embodiments, the processing subsystem 110 may one or more additional components 118 (e.g., one or more microphones, cameras, Global Positioning System (GPS) sensors, Near Field Communication (NFC) sensors).

In some embodiments, the processing subsystem 110 may include one or more components partially or wholly incorporated into the sensor module 101. In other embodiments, however, the processing subsystem 110 may include components remote from the sensor module 101 and connected thereto by a communication network (e.g., the Internet and/or another network). In some embodiments, for example, at least a portion of the processing subsystem 110 may reside on a mobile device (e.g., a mobile phone, a tablet, a personal digital assistant) and/or a computer (e.g., a desktop computer, a laptop) communicatively coupled to the sensor module 103.

Suitable Methods

Figure 2:
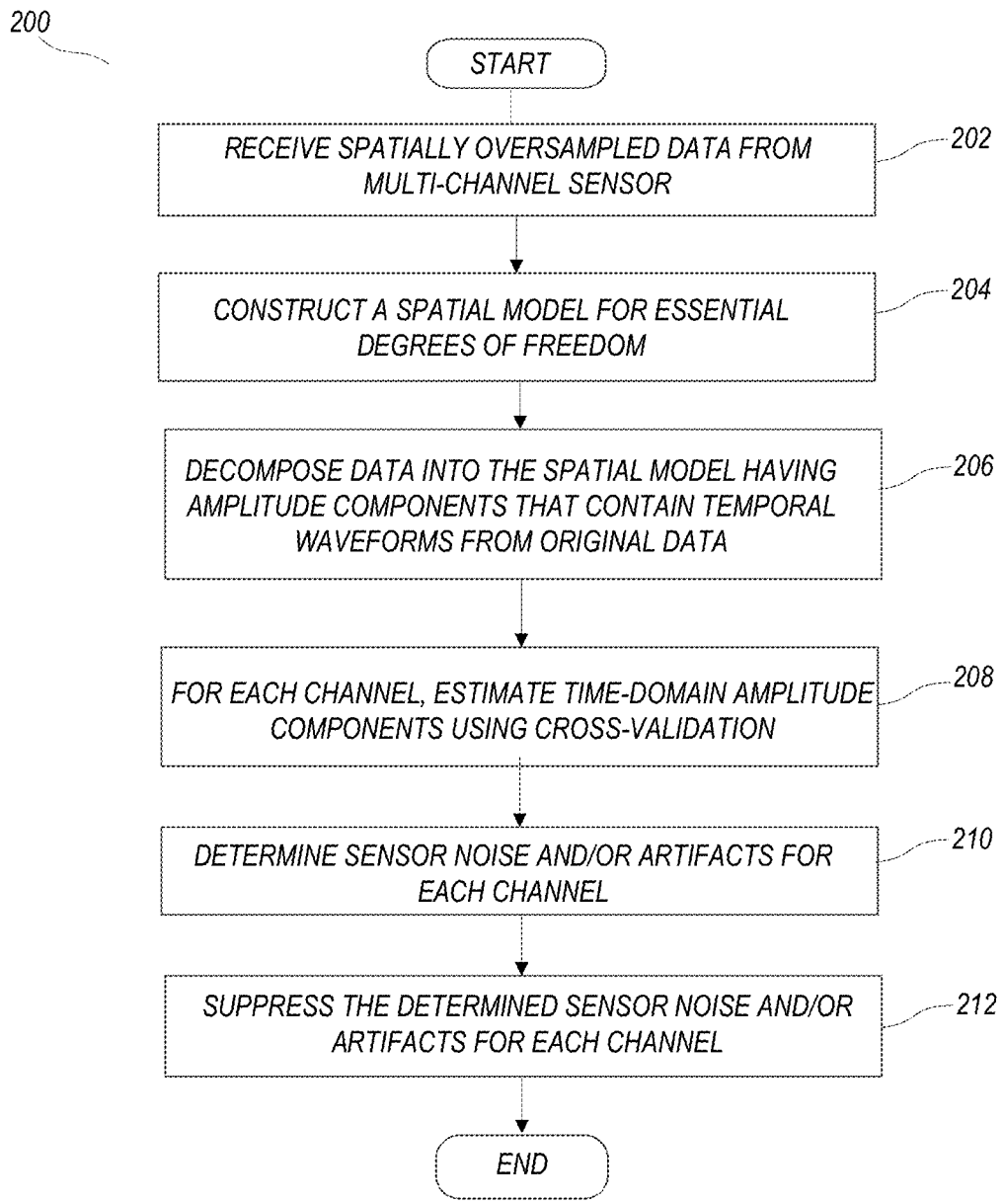
FIG. 2 is a schematic diagram of the process flow for suppressing sensor noise for a multi-channel sensor system in accordance with embodiments of the present technology.

FIG. 2 is a flow diagram of a process 200 configured in accordance with an embodiment of the present technology. The process 200 can include instructions stored, for example, in the memory 111 of the system 100 (FIG. 1) that are executable by the one or more processors 112 (FIG. 1). In some embodiments, portions of the process 200 are performed by one or more hardware components (e.g., the sensor module 101 of FIG. 1). In certain embodiments, portions of the process 200 are performed by a device external to the system 100 of FIG. 1.

At block 202, the process 200 receives spatially oversampled data from the multi-channel sensor (e.g., the sensor module 101 of FIG. 1). In one example, the data can be MEG data recorded over a period of time from an array of MEG sensors disposed over a patient's head, for example 300 or more individual MEG sensors. The data includes a plurality of individual channels, for example in some embodiments one channel per individual sensor.

At block 204, the process 200 constructs a spatial model for essential degrees of freedom for the data obtained in block 202. At block 206, the process 200 continues by decomposing the data into the spatial model. The spatial model has amplitude components that contain temporal waveforms from the original data obtained in block 202. In some embodiments, for example, the spatial model can be built by implementing a combination of a basic solution of Laplace's equation for the harmonic scalar potential, taking the corresponding gradient, and thus determining the magnetic field in the measurement area to calculate a spatial basis. In certain embodiments, the spatial model is built using dominating spatial patterns found in a statistical analysis of the original data to calculate a spatial basis, for example using dominating spatial patterns found in a principle component analysis.

At block 208, the process 200 estimates time-domain amplitude components using cross-validation for each channel, and at block 210, the process 200 determines the sensor noise and/or artifacts for each channel. Once identified, the process 200 suppresses the sensor noise and/or artifacts for each channel.

In some embodiments, sensor noise and/or artifacts are suppressed by applying an orthogonal projection operator, while in other embodiments a parallel projection operator is used. In one example, identifying and suppressing sensor noise and/or artifacts can include decomposing the data in two situations for each channel of the multi-channel device. In the first situation, the amplitude components are estimated when applying the spatial model to all channels, while in the second situation, the amplitude components are estimated when applying the spatial model with the channel under investigation excluded from the data and the spatial model. Next, the results of the first situation and the results of the second situation can be compared, with the difference indicating the sensor noise and/or artifacts for the channel under investigation. This process can be repeated for each channel to identify sensor noise and/or artifacts for each individual channel. In some embodiments, the results are compared using an orthogonal projection operation. In some embodiments, the results are compared using a singular value decomposition of the temporal domain signals of the amplitude coefficients corresponding to the spatial model to find a temporal basis.

In another example, the sensor noise and/or artifacts are identified and suppressed by applying the spatial model with the channel under investigation excluded from the data and the spatial model. The difference in the temporal domain between the decomposition and the original data for the channel under investigation can indicate the sensor noise and/or artifacts for the channel under investigation. To suppress the identified sensor noise and/or artifacts, a temporal waveform common to the channel under investigation and the decomposition can be found. In some embodiments, the common temporal waveform can be found by projecting the original channel waveform to a temporal basis spanned by the decomposed amplitude coefficients by a parallel projection operator. The parallel projection operator can be a singular value decomposition of the temporal domain signals of the amplitude coefficients corresponding to the spatial model to find the temporal basis.

In some embodiments, the spatial model can be constructed as outlined below. For an instance of a multichannel measurement instrument with N independent measurement channels that essentially detects signals belonging to a signal subspace with n<N degrees of freedom (i.e., a spatially oversampled measurement system), a multichannel data matrix D of N channels (rows) and $n_s$ temporal samples (columns) can be defined as:

$$D = M_a X_a + M_b X_b + E_u + E_c \quad (1)$$

Here $M_a$ and $M_b$ are N×na- and N×nb-dimensional matrices defining the detectable subspaces for signals of interest and externally produced interference, respectively, such that $n_a + n_b = n$. $X_a$ and $X_b$ are the corresponding $n_a \times n_s$- and $n_b \times n_s$ dimensional coordinate matrices. For example, $M_a$ could be a brain-to-sensor physical mixing model in MEG and $M_b$ could span magnetic fields produced by environmental or biological, such as heart, interference sources. However, embodiments of the present technology are particularly useful in addressing the role of uncorrelated sensor noise without considering external interference or the existing algorithms that effectively suppress it, e.g., signal-space projection (SSP), signal space separation (SSS), or time-shift principal component analysis (tsPCA). Therefore eq. 1 can be simplified by making the substitutions $M = [M_a \ M_b]$ and $X = [X_a^T \ X_b^T]^T$, which leads to:

$$D = MX + E_u + E_c \quad (2)$$

Thus, $D_0 = MX$ is the noiseless signal that can be modeled with an overdetermined spatial model. In some embodiments, the assumption can be made that cross-talk between channels is negligible or has been compensated for mathematically using other processes.

There are two $N \times n_s$-dimensional noise matrices:
1) $E_u$ contains spatially uncorrelated artifacts and individual sensor noise. The corresponding covariance matrix $C_u = E[E_u E_u^T]$ is diagonal (E indicates expectation).
2) $E_c$ contains spatially correlated artifacts that are not spanned by matrix M. For example, radiation shield noise or common-mode artifacts caused by the measuring instrument itself typically belong to this category.

For the sake of simplicity, $E_c$ can be set to 0 in the sensor noise investigations addressed herein. Regarding modeling error, if M is composed of basis functions spanning the signal distributions of interest, it is often possible to construct M in such a way that the modeling error is negligible. The quasistatic magnetic field, for example, can be expressed with a rapidly converging series of spherical harmonic basis functions that allows one to express the measured signals with a relatively small number of degrees of freedom, that is, number of columns in M. Thus, model in eq. 1 reduces to $$D = MX + E_u \quad (3)$$

As noted previously, spatial operators for noise-suppression have been identified, and examples of such spatial operators are outlined in more detail in Appendix A. However, there are several benefits to employing a temporal operator for sensor noise suppression using cross-validation.

Traditionally, the approaches for sensor noise suppression are formulated with the spatial domain as the starting point. However, CV operators can also be constructed by considering signals in the temporal domain. The simplest formulation is perhaps the channel-wise time domain-parallel projection $$\tilde{d}_j = d_j V_{\notin j} V_{\notin j}^T \quad (4)$$

where $d_j$ and $\tilde{d}_j$ are the original and sensor-noise-suppressed $1 \times n_s$ signal vectors, respectively, of channel j, and $V_{\notin j}$ is the orthonormal temporal subspace derived from all channels excluding channel j itself. The set denoted as $\notin j$ could also correspond to a smaller subset of channels excluding j, as long as the number of channels in this subset would exceed n and properly sample the temporal subspace.

The main question in the temporal-domain cross validation is how to determine the signal subspace $V_{\notin j}$. There are many such potential formulations, but the simplest is perhaps given by right singular vectors of $D_{\notin j}$:

$$D_{\notin j} = U_{\notin j} S_{\notin j} V_{\notin j}^T, \quad (5)$$

with the orthonormalized temporal waveforms of $D_{\notin j}$ being represented in the rows of matrix $V_{\notin j}^T$.

This simple formulation results in a relationship between the temporal formulation of sensor noise suppression via OTP to the SNS method's $K_{SNS}$ operator matrix. Coefficients for $K_{SNS}$ are derived from the principle component analysis (PCA) of the data. The eigenvectors A and eigenvalues $\lambda$ from PCA are related to the left singular vectors and singular values as $A = U^T$ and $\lambda = \text{diag}(S)^2$, respectively. In other words, SNS uses the singular values alongside the left singular vectors of the original data matrix D to create its operator, whereas OTP uses the right singular vectors.

However, this basic temporal formulation based on right singular vectors actually gives rise to an equivalent spatial operation. A closer look at eq. 5 shows that $V_{\notin j}^T = S_{\notin j}^{-1} U^T D_{\notin j}$, so combined with eq. 4, it can be seen that $$\tilde{d}_j = (d_j D_{\notin j}^T U_{\notin j} S_{\notin j}^{-1} S_{\notin j}^{-1} U_{\notin j}^T) D_{\notin j} = \kappa_j D_{\notin j}$$

The matrix multiplications can thus be collapsed to a single $1 \times (N-1)$ matrix of coefficients $\kappa_j$ that are used to multiply $D_{\notin j}$ to obtain $\tilde{d}_j$. These coefficients $\kappa_j$ can be trivially inserted row-by-row (leaving zeros on the diagonal) to itself form a spatial operator $K_{OTP}$ where $\tilde{D} = K_{OTP} D$. Thus, this basic time-domain investigation leads to a spatial cross-validation matrix when singular value decomposition (SVD) is used to determine the waveforms. In fact, any linear decomposition method operating on the data matrix D will similarly result in a spatial operator.

The temporal operator can be improved with an appropriate estimate of the model parameters M. For example, for MEG data, the physical relationship between the sources of interest and sensors can be used to create the regularized multipole moment basis also used by SSS. This can then be used to reduce the matrix as $M_{\phi j}D_{\phi j}$ prior to computing the right singular vectors for $d_j$ projection. This is referred to herein as variant $OTP_{SSS}$.

Both SNS and OTP can be formulated to operate on a given data matrix D in a single pass, or by processing data in chunks of $n_{seg}$ samples (with $N<n_{seg}<n_s$). A simple constant overlap-add (COLA) approach can be used to minimize edge artifacts using a Hann window with 50% overlap. This gives rise to a single algorithm parameter, namely the processing window duration. Within each window, the algorithm proceeds according to eq. 4. For numerical reasons, in practice it can be useful to rescale channels to a similar scale before processing, and also demean the data before computing the right singular vectors $V_{\phi j}$.

When applied to Elekta Neuromag® MEG data (306 channels, 1000 Hz sample rate) this type of algorithm can operate roughly 3 times slower than realtime. Using a non-identity basis M, such as in $OTP_{SSS}$, can reduce computation time by a factor roughly equivalent to the rank reduction of the data (e.g., 306 channels to 88) would yield roughly a 3× speedup over the identity version). Note that the rank of 88 is just an example related to the initial rank of the full SSS basis, typically 95, followed by regularization to optimize the numerical stability of the basis.

As noted above, multichannel data can be roughly divided into contributions from the object of interest, interference sources common to the sensor array, and intrinsic sensor noise and artifacts arising from the sensors themselves. While the spatially correlated part of the signal can often be processed with deterministic signal models, the momentary contributions of intrinsic sensor noise and artifacts are unpredictable even though one may have some statistical information about them. In case of oversampling, that is, with a sensor array containing more measurement channels than degrees of freedom in the detectable signal with spatially correlated structure, one can use CV (leave one channel out at a time) techniques for estimating the intrinsic sensor noise and artifact contribution. The methods outlined herein are based on CV with the components of the sensor noise suppression methods derived in the temporal rather than in the spatial domain. The spatial domain approach has been demonstrated before, but the temporal approach has certain advantages that may be useful, e.g., in clinical MEG work. Another way to compensate for the effects of sensor noise and artifacts is to take their contribution into account in regularized projections of the measured data onto signal models. Such methods include, e.g., Wiener filtering, signal space projection, or matrix inversions with incorporated noise covariance estimates. However, sensor-level noise suppression facilitates visual inspection of raw data while suppressing the noise of the associated noise estimates. In addition to introducing the specific framework of sensor noise suppression derived in the temporal domain, the mathematics of CV-based sensor noise suppression are described with sufficient depth to facilitate understanding of the subsequent characteristics of the processed data.

The benefit of spatially derived CV is that in the process of estimating each channel signal exclusively from all other channels but the channel itself, it is evident that each channel has its own sensor noise and artifact contribution completely removed. The disadvantage of this approach is, however, that it is difficult to control for inter-channel spreading of sensor noise and artifacts in this framework. As a consequence, while decreased in amplitude, the intrinsic sensor noise is redistributed among channels in this operation. Another potential complication of the spatial model is that, depending on the implementation, the subsequent source modeling may require compensation against the spatial bias produced by the spatial sensor noise suppression operator. Testing has established that such compensation cancels the effect of sensor noise suppression in the source space.

Testing has demonstrated that the temporal domain projection provided by the OTP method is an efficient way to suppress intrinsic sensor noise without causing significant spreading of sensor noise and artifact contributions between channels, which is an important practical benefit. The main consequences are that the users of the technique do not manually have to specify any bad channels to be excluded from the data, the risk of misinterpretation of data is mitigated due to the insignificant spreading of intrinsic noise, and there is no need to compensate for the sensor noise suppression operation in source models. As noted above, certain embodiments of the present technology do assume statistical independence and linear algebraic orthogonality. Whether these assumptions hold true on a case-by-case basis is a statistical question that requires practical evidence and experience. As described below, data has been obtained from seven different MEG sites, recorded at a large range of amplitudes (20 nAm to 500 nAm), and the results consistently show improvements using OTP.

OTP provides the best combination of simultaneously providing satisfactory sensor level noise suppression and ensuring minimal spatial bias of the signal of interest. Therefore, OTP does not require lead field level compensation, which would leave to compromised suppression of random noise in the source space. Moreover, using a non-identity basis M, such as the SSS-based matrix used here, can yield additional improvements. Additionally, the window duration parameter of OTP provides a tradeoff that can be set based on the data of interest. At the long-window extreme, the suppression factors are the largest. At the short-window extreme, the OTP technique adapts well based on time-varying sensor structure and quality, better compensating for non-stationarity in the data. In practice for MEG data, 10 second windows appear to provide the best compromise.

The simplest formulation of the OTP operator can be expressed as a matrix multiplication of an N×N-dimensional spatial matrix and the original data if the temporal subspace of interest is derived by a simple SVD algorithm. Under this formulation, OTP could also result in some inter-channel artifact spreading in some particularly difficult cases, even if it is designed to be minimized by the right singular vector computation and subsequent projection. However, OTP as a general framework provides opportunities for extension to address these sorts of issues. For example, within a given window, the uncorrelated sensor noise and artifact patterns can be estimated, yielding an N×$n_s$-dimensional "random noise" matrix. A small number of dominating waveforms of this matrix may then be selected and projected out from the original data. The most significant channel artifacts are thus suppressed from the data by an overall temporal domain projection, i.e., by applying the same projection, which contains the worst channel artifacts, to all channels at once. As a consequence, the artifact spreading introduced by the aforementioned spatial matrix multiplication, which is already designed to be minimized by OTP, is even less significant with the data that have been pre-cleaned with respect to the worst artifacts.

Suppression of sensor noise also opens up the opportunity for applications in areas where the signal of interest is known to be low with respect to the intrinsic sensor noise. An example of such an application area is the analysis of high-frequency oscillations (HFO) in MEG. The HFO signals may be higher in frequency than most of the environmental interference, rendering the intrinsic sensor noise the dominating noise contribution in the HFO frequency band. This topic is especially relevant in epilepsy where the HFO contribution is believed to convey very important information about the seizure onset area and while HFO is visible in intracranial recordings, it is difficult to detect in a non-invasive fashion with present SNR levels.

Test Cases

Several illustrative cases are provided below to demonstrate the usefulness of the noise-suppression techniques enabled by the present technology. Performance of OTP against SNS was tested using the PCA-based formulation described above. Processed data was also tested with the STAR algorithm (using the software package NoiseTools, version 18 Nov. 2016), which applies a statistical thresholding procedure to correct artifacts timepoint-by-timepoint using an SNS-like procedure.

For illustrative purposes, signal space separation (SSS) as implemented in MNE was also used, which acts as a linear spatial operator to suppress external interference artifacts. Note that SSS is not a sensor-noise removing algorithm, but is rather designed to suppress environmental artifacts. It is shown here only as an example of preprocessing spatial operators that could be applied to data, and without loss of generality.

1. Phantom and Empty-Room Data

Phantom MEG data were recorded at six sites equipped with an Elekta Neuromag® or Triux®MEG system: the University of Washington (UW) at 500 nAm, Massachusetts General Hospital (MGH) at 500 nAm, the Epilepsy Center at the Cleveland Clinic Neurological Institute at 20 and 200 nAm, Minamata at 500 nAm, BioMag Laboratory at Helsinki University Central Hospital at 500 nAm, and at the Otaniemi site of Aalto University at 20 and 100 nAm. The data from Cleveland Clinic were obtained as part of the informative and publicly available BrainStorm tutorials. Elekta Neuromag® MEG systems contain 306 MEG sensors, consisting of 102 magnetometers and 204 planar gradiometers (in orthogonal pairs). Phantom data were acquired with an MEG phantom with 32 controllable dipoles at fixed, known locations and orientations. All 32 dipoles were used for UW, Cleveland, BioMag, and Minamata, with 27 used for MGH and 28 for Otaniemi based on reliable localization. Only the 200 nAm Cleveland data are shown here because the 20 nAm data did not produce reliable single-trial localization. For each recording, before placing the phantom in the MEG room, head position indicator (HPI) coils were attached, and the HPI locations and cardinal landmarks (nasion, left/right periauriculars) were digitized with a 3Space Fastrak (Polhemus). The phantom was placed inside the MEG helmet and coregistered to the MEG sensors using the HPI coils. The phantom then repeated brief two-cycle sinusoidal pulses from each dipole.

Data were also recorded at Boston Children's Hospital (BCH) on the Tristan Systems BabyMEG system with 270 magnetometers, 105 compensation magnetometers, 9 reference magnetometers, and a custom phantom with 6 usable dipoles at 200 nAm. A separate set of over 300 trials of 20 nAm were used to empirically determine veridical dipole locations in head coordinates for use with the 200 nAm data. The device-to-head coordinate frame transformation for the BabyMEG system was determined by doing a nonlinear quaternion fit of a transformation matrix between the veridical dipole locations and the empirical locations also using many trials (over 300 per dipole).

Figure 3:
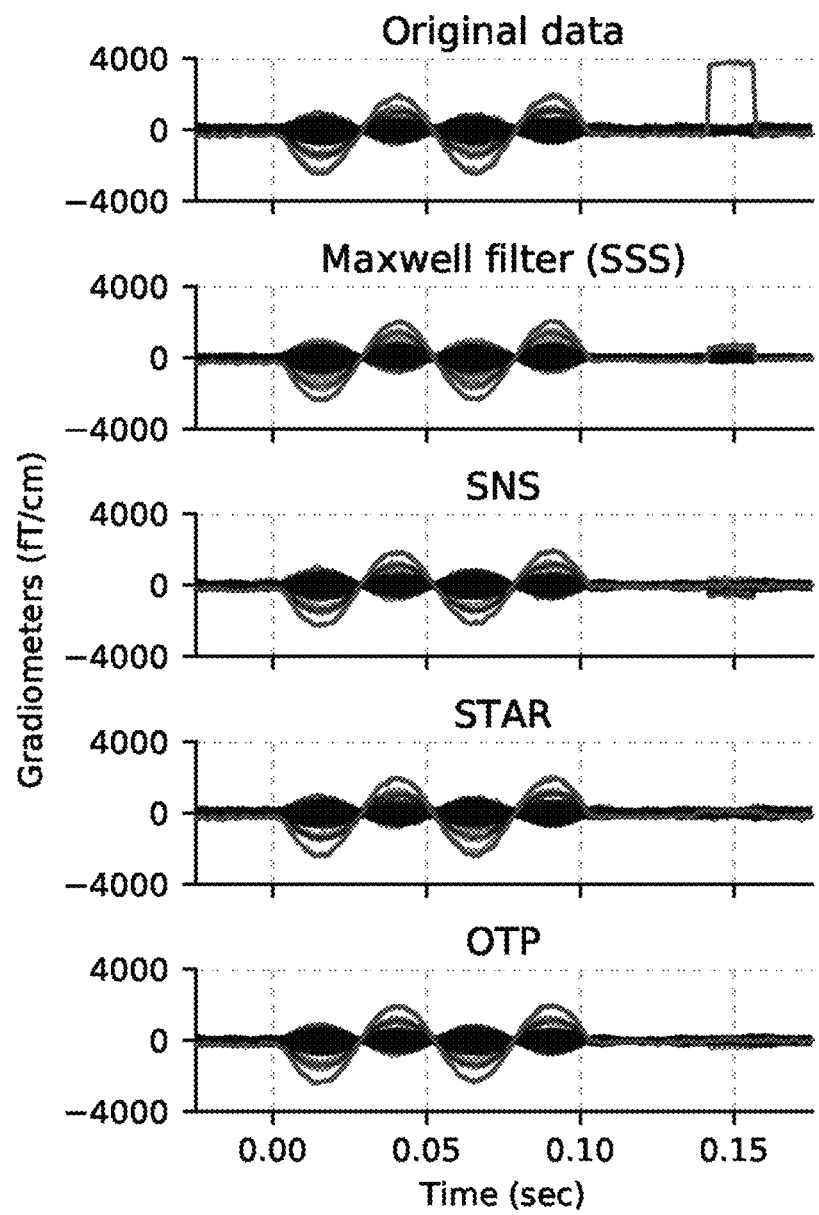
FIG. 3 illustrates examples of various noise-suppression techniques operating on exemplary original data.

To emulate a strong jump artifact, a 4000 fT/cm amplitude 15 ms rectangular jump artifact was added to a single MEG gradiometer (2422) which exhibited a strong response (based on visual inspection) to the first epoch of the first phantom dipole in the UW phantom recording. This data had a high SNR (25 dB) 20 Hz sinusoid power on gradiometers compared to baseline. This artifact was present only for visual demonstration purposes (FIG. 3), and was not present during source localization.

Phantom data were processed with OTP, STAR, and/or SNS. STAR processing used NoiseTools version "18 Nov. 2016" and default options. SNS processing used the version implemented in the MNE sandbox (https://github.com/mne-tools/mne-sandbox; commit 1d050dc) as it consistently outperformed the NoiseTools implementation for these data. For each recording, data were processed by these techniques without excluding bad channels, except for BCH data, where 247 of the 270 available magnetometers were used (and all 114 reference magnetometers were ignored).

Phantom dipoles were localized for these processed (and raw) data by using a fairly simple processing pipeline: 1) zero-phase FIR notch filtering at line frequencies (50 or 60 Hz plus harmonics) if necessary (plus band-pass filtering between 2 and 50 Hz for BCH); 2) excluding bad MEG channels based on visual inspection for Aalto (2233, 1211, 0511, 2142, 2422, 2231), BioMag (1013), UW (0441, 1913, 2611), Cleveland (1423, 1522, 2413, 2421), MGH (none), Minamata (none), and BCH (150); 3) epoching the data at the onset of each dipole activation; 4) throwing out epochs that exceeded lenient thresholds (10000 fF/cm for gradiometers, 40000 fT for magnetometers); 5) averaging across epochs; 6) computing sensor covariances using the baseline period; 7) regularizing covariances to deal with rank deficiency (e.g. SNS at low neighbor counts); 7) performing a single dipole fit at the peak of the phantom dipole activation using a spherical conductor model with center at the head origin.

Note that this pipeline involves very little effective environmental denoising; only the filtering and whitening via covariance during dipole fitting reject some of the environmental noise. So the dipole fits recorded here for each site should not be considered an optimal representation of data quality for any given site.

For SNS, optional compensation of dipole fits ($SNS_{COMP}$) was performed by multiplying the lead fields during fitting by the same spatial operator that was used to denoise the channels. Although in principle SNS and OTP are designed to correct the bad channels above, here they are omitted so that the original, SNS, and OTP localization procedures operate on equivalent datasets. For each site, the average across 10 single-dipole fits for each dipole was used to assess the localization bias.

Empty-room data were acquired with no subject present in the MEG room for a duration of approximately 121 seconds at UW. After the recording, data were visually inspected and six MEG channels (0142, 0413, 0442, 1442, 1722, and 2643) were identified as having clear channel-specific artifacts. This is more than is typical in an MEG recording, but this recording was selected to demonstrate various kinds of MEG channel artifacts.

Single-subject MEG data during an audio-visual experiment were also analyzed from the publicly available MNE-Python "multimodal" dataset, which was recorded at Otaniemi using left and right auditory stimuli, somatotopic stimulation, and visual upper/lower left/right stimuli.

2. Synthetic Data

Independent identically distributed (IID) zero-mean, unit standard deviation Gaussian sensor noise data were generated (using a standard Mersenne Twister from NumPy) for each of the 306 MEG channels for 60 seconds of data. The temporally white signals were then also processed them with an autoregressive IIR filter (numerator [1], denominator with coefficients [1, −1, 0.2]) to approximate temporally pink noise. Shot-like noise was simulated by scaling the white noise by 0.001 and randomly adding unit impulses to channels (at most one per channel at any given time) at an approximate rate of 1 Hz per channel.

Suppression levels for OTP and SNS in decibels (dB) were then calculated as $$20 \log_{10}\left(\frac{\|D\|}{\|\tilde{D}\|}\right). \tag{6}$$

The suppression factors were calculated in source space by using a simplified dipole fitting routine to estimate "neural currents" (in nAm) in source space. To estimate these, for each of the 32 Neuromag phantom dipole locations and orientations (which have a reasonable spatial sampling), the inner product between the lead field vector for that dipole and the sensor space data was taken. This is mathematically equivalent to standard fixed-position, fixed-orientation single equivalent-current dipole (ECD) amplitude estimation, given that the sensor noise covariance is a diagonal with equivalent values per channel. Suppression could then be measured in this 32-dipole source space by using the same metric as in sensor space. By estimating the neural currents for this simulated data, which by construction contains only IID sensor noise, it can be determined how well such sensor noise would be suppressed during the source estimation process if there were actually neural signals present in the data.

3. Results

First, a condition was simulated that could be problematic especially with the interpretation of clinical MEG recordings: a single channel contains a temporal artifact (e.g., from flux trapping) that spreads to other channels when processed using spatial methods. A brief 15 ms rectangular pulse was added into a single gradiometer channel of a recording of an MEG phantom, which repeatedly activates a dipole, with results shown in FIG. 3. The top row shows phantom dipole activation (2-cycles of 20 Hz sinusoid) across channels combined with a simulated channel artifact (square pulse) on a single gradiometer channel of a similar magnitude to the phantom activation. Spatial methods such as Maxwell filtering (SSS; second row) and SNS (third row; $N_{neighbors}$=305) spread the artifact across channels, conferring a spatial profile to the artifact, whereas STAR (fourth row) and OTP (bottom row; 30 sec duration) remove the artifact from the data without compromising the other channels. Although SSS is not designed to remove individual sensor noise, it is a representative example of a spatial filter commonly used on MEG data to suppress environmental noise.

Figure 4:
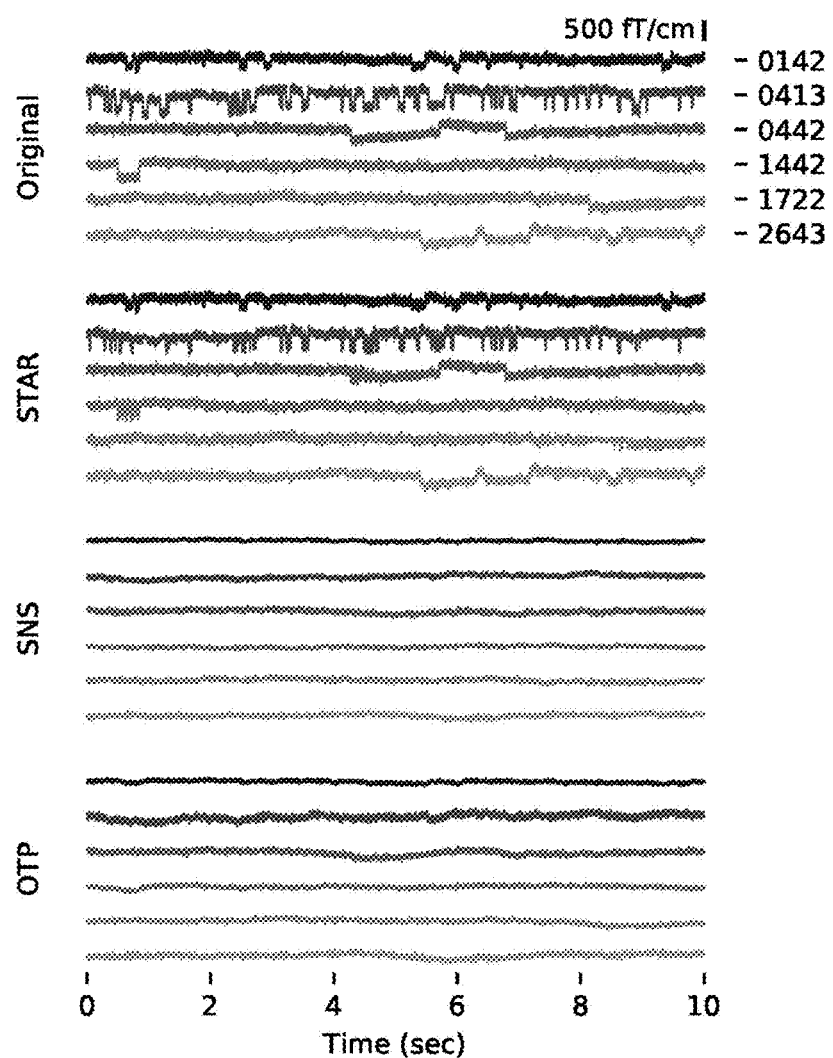
FIG. 4 illustrates examples of suppressing non-correlated sensor artifacts using various noise-suppression techniques.

Next, the examined data was recorded with no subject present, which is often called "empty-room" data. This recording contained a handful of channels with clearly visible sensor-noise artifacts. In each case, the visible temporal artifacts in the data were greatly suppressed by both OTP and SNS (as shown in FIG. 4), while only a subset were suppressed by STAR. FIG. 4, for example, illustrates how uncorrelated sensor noise artifacts are suppressed by OTP and SNS. Temporal artifacts that are restricted to individual channels (top) are partially removed by STAR (second row) and effectively suppressed by SNS (third row; $N_{neighbors}$=305) and OTP (fourth row; 30 second duration).

Figure 5:
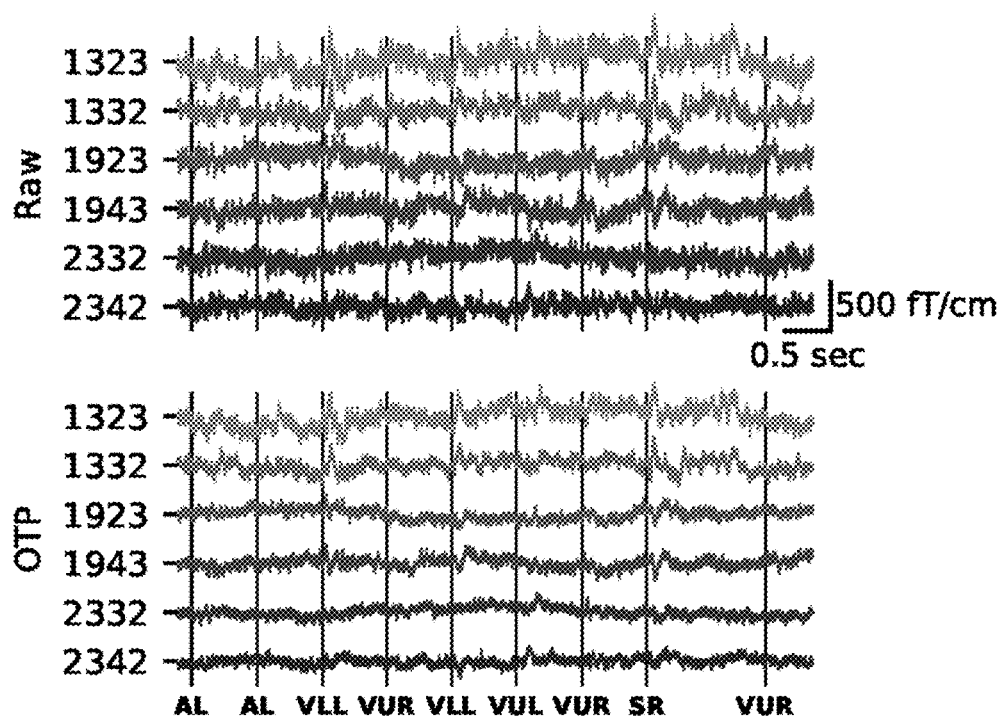
FIG. 5 illustrates an example of results of an oversampled temporal projection (OTP) noise-suppression operation on raw data.

In addition to correcting artifacts, OTP can also be used to improve visual inspection of evoked data. An example of 10 seconds of raw data from a single-subject, multi-sensory MEG experiment is shown in FIG. 5. As shown in FIG. 5, data from an example multi-sensory experiment show examples of how OTP can improve single-trial evoked response visibility, with trial types auditory left (AL), visual lower left (VLL), visual upper right (VUR), visual upper left (VUL), and somatotopic stimulation right (SR), before (top) and after (bottom) denoising with OTP. This optimal window-size tradeoff might depend on the given sensor configuration and sensor noise characteristics, and thus could be domain or system dependent. The sensor denoising makes single-trial responses (e.g., to somatosensory stimulation) more prominent when browsing raw data.

Figure 6:
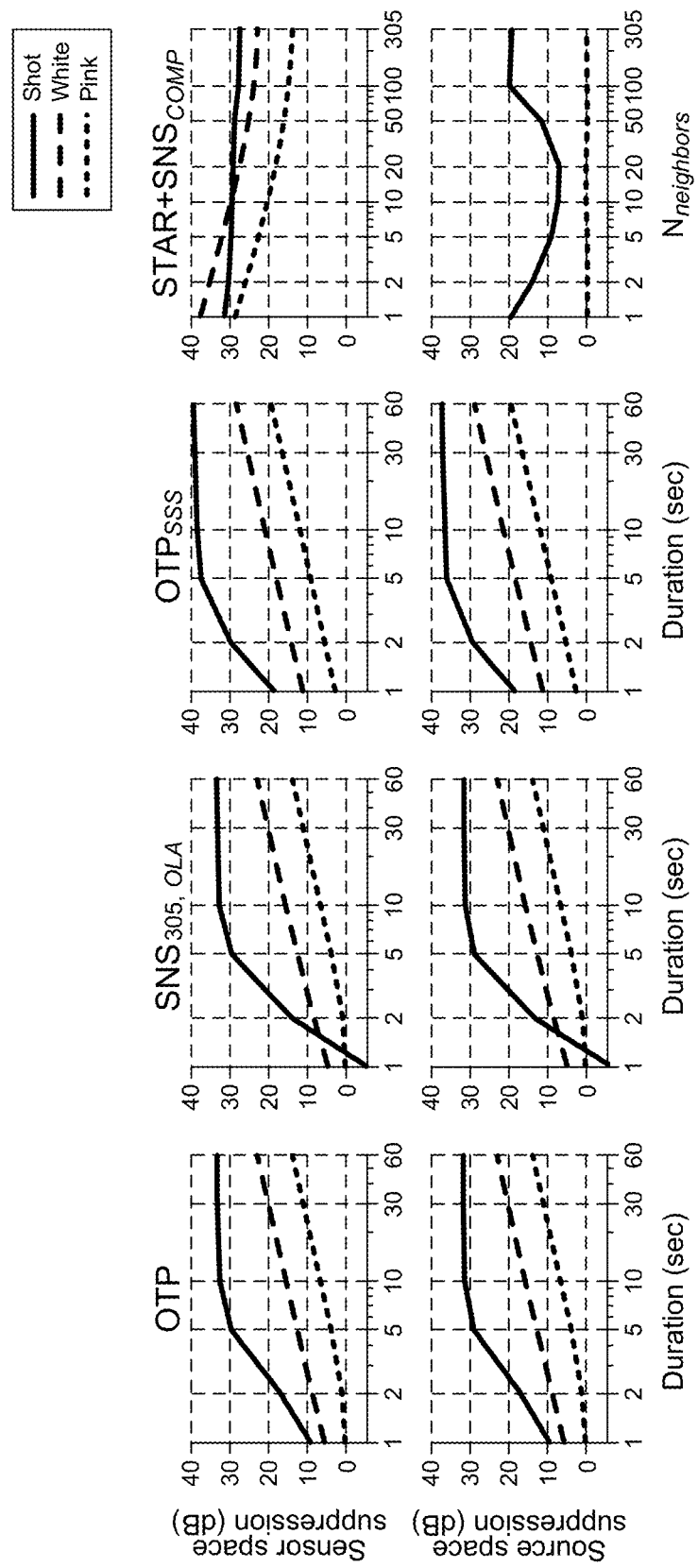
FIG. 6 illustrates various examples of source space and sensor space suppression with different noise-suppression techniques.

Using simulated data, the suppression of idealized sensor noise for data both in sensor space, and in source space (i.e., during source localization) was quantified. Independent noise was generated for 306 signals, analogous to the 306 sensors in the Elekta Neuromag® MEG acquisition system. Next, signals with white (flat) and approximately pink (1/f frequency falloff) temporal spectra were used, as well as data with shot noise processes. SNS and OTP were applied with varying $N_{neighbors}$ and duration, respectively. In sensor space, OTP and SNS have matching suppression levels when OTP uses the entire duration (here, 60 seconds) and SNS uses the maximum $N_{neighbors}$=305. For example, FIG. 6 illustrates how OTP suppresses simulated independent noise in sensor and source space. As shown, OTP using an identity matrix (first column) shows slightly better performance than SNS applied in an overlap-add scheme ($N_{neighbors}$=305; second column) at short durations, but otherwise has similar performance in both sensor (top row) and source space (bottom row) for three noise types: shot noise (solid lines), white noise (dashed lines), and pink noise (dotted lines). A reduced-rank SSS basis (third column) shows slightly better suppression. Although STAR followed by standard SNS (fourth column) has good noise suppression in sensor space, applying compensation in source space eliminates the noise reduction for pink and white noise, and reduces it for shot noise.

The suppression factor of SNS drops effectively to zero for white and pink noise in source space during localization when the lead fields are properly compensated, whereas OTP suppression remains at the same levels as in sensor space. However, when SNS is used to compute coefficients for overlap-add operation ($SNS_{305,OLA}$), suppression is similar to that of OTP, and is maintained in source space. OTP can also be modified to use a rank-reduced basis for projection, termed $OTP_{SSS}$, to obtain modest gains in suppression factors in sensor and source space.

Figure 7:
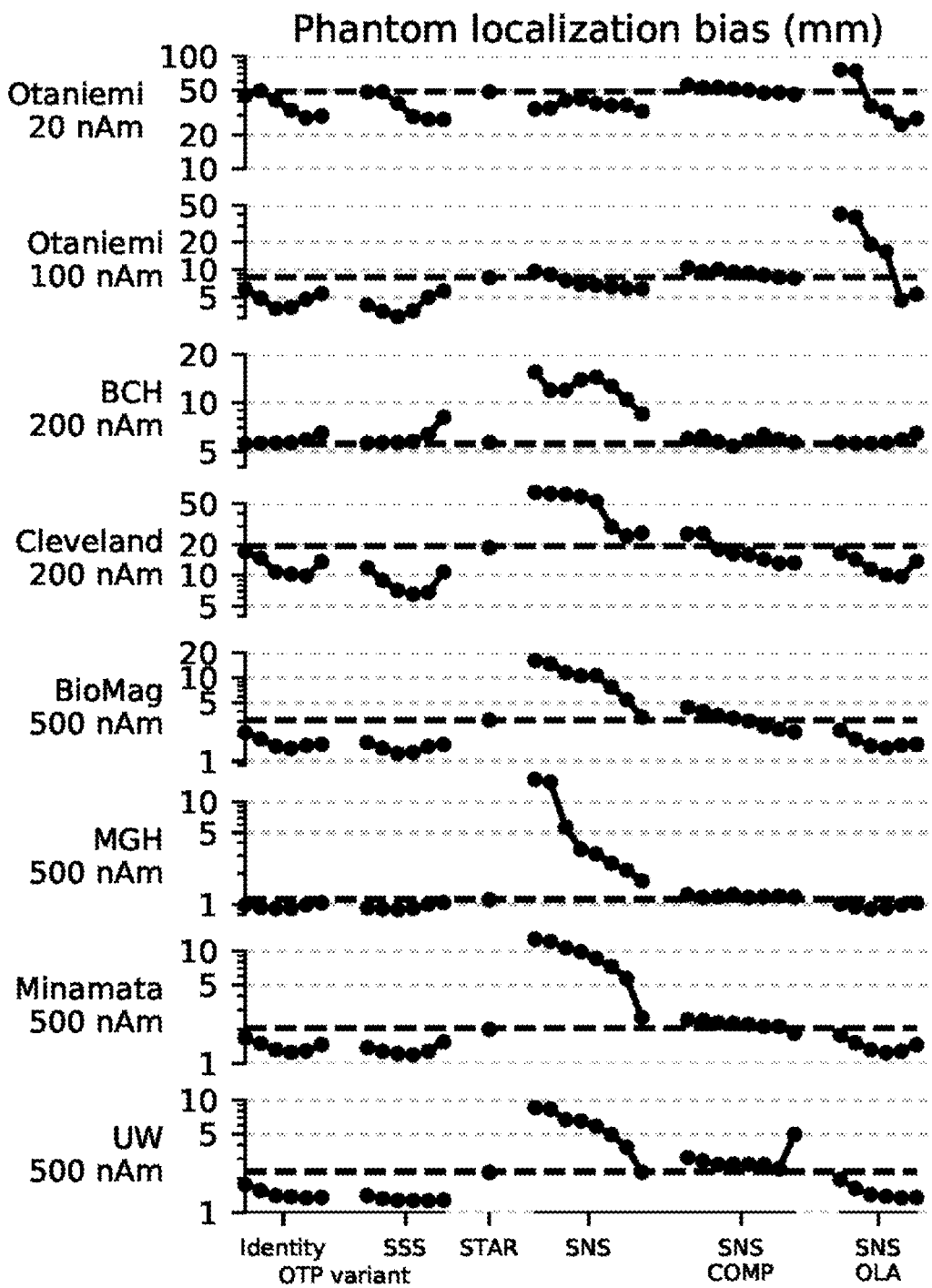
FIG. 7 illustrates various examples of reducing localization bias using different noise-suppression techniques.

The tests also examined the effect of OTP on source localization using experimental data from MEG phantoms from seven sites by measuring single-trial equivalent-current dipole (ECD) localization error. For example, FIG. 7 illustrates how OTP reduces localization bias in recorded data. As shown, localization bias (y-axis, log scale) averaged across 10 single-trial localizations of phantom dipoles for five different sites (with 20 nAm and 200 nAm recordings from Otaniemi), with unprocessed data localization shown for each site (dashed black lines). Two OTP variants are shown using an identity matrix (left) and reduced-basis (right; SSS), with minor variations in performance across durations (dots: 1, 2, 5, 10, 30, and 60 seconds). The improvement for OTP also changes as a function of window duration, with an optimal value generally around 10 seconds. STAR alone had no discernable effect on localization. STAR followed by SNS and SNS alone performed very similarly, so only SNS is shown ($N_{neighbors}$: 1, 2, 5, 10, 20, 50, 100, and 246 [BCH] or 305 [all others] as sequential dots). SNS usually biases localization, but lead-field compensated SNS processing approximately restores bias to the level of unprocessed data. When applied in an overlap-add windowed processing scheme, SNS approaches standard OTP performance for some but not all sites (e.g., not Otaniemi at 20 or 100 nAm). Overall, the SSS variant of OTP shows the best performance.

OTP, which required no compensation of the lead fields during fitting, typically reduced the localization bias relative to unprocessed data (especially for the 10 second duration), with long durations sometimes leading to a slight bias increase (e.g., 60 seconds for BCH). STAR had no discernable effect on localization for any site. SNS, if no lead field compensation was applied, generally increased the localization bias, particularly when $N_{neighbors}$ was small (in some cases increasing errors by an order of magnitude). When the operator was applied to the lead field during fitting, SNS typically converged to the same localization error as the unprocessed data. One interesting exception is the Cleveland data, where the compensated SNS showed a reduction in localization bias, although it still had larger bias than OTP; for this data in the $N_{neighbors}=20$ condition, the SNS operator matrix discarded 16.6% (51 of 306) of the channels. When SNS was applied in an overlap-add scheme, localization was usually similar to OTP, but worse for some sites (e.g., Otaniemi). The reduced-rank version $OTP_{SSS}$ had the lowest localization bias overall.

As explained above, and as demonstrated by the above test cases, sensor noise in multichannel arrays that provide spatial oversampling can be effectively suppressed using OTP, a leave-one-out cross-validation method with temporal projection using overlapping windows. The relevant mathematical properties of sensor noise suppression operators have been derived in both sensor space and during source localization. Finally, illustrative studies have demonstrated that OTP is expected to provide superior performance compared to existing methods, especially during localization of the generators that give rise to the sensor-level signals.

EXAMPLES

1. A multi-channel sensor system, comprising:
   a multi-channel sensor configured to obtain spatially oversampled data; and
   a computing device communicatively coupled to the multi-channel sensor, the computing device configured to—
   (a) receive the spatially oversampled data from the multi-channel sensor;
   (b) build a spatial model from the data for essential spatial degrees of freedom;
   (c) decompose the data into the underlying spatial model to obtain associated amplitude components containing a mixture of original temporal waveforms of the data;
   (d) for each channel of the multi-channel sensor, estimate time-domain amplitude components using cross-validation;
   (e) for each channel, based on the estimated time-domain amplitude components, identify sensor noise and/or artifacts for that channel; and
   (f) for each channel, suppress the identified sensor noise and/or artifacts from the data.

2. The system of example 1 wherein the multi-channel sensor comprises at least one of: a magnetoencephalographic (MEG) sensor array or an electroencephalographic (EEG) sensor array.

3. The system of any one of examples 1-2 wherein the computing device is configured to decompose the data into the underlying spatial model by decomposing the data in two situations for each channel of the multi-channel sensor device, the two situations including:
   a first situation in which the amplitude components are estimated when applying the spatial model to all channels; and
   a second situation in which the amplitude components are estimated when applying the spatial model with the channel under investigation excluded from the data and the spatial model; and
   wherein the computing device is further configured to estimate the time-domain amplitude components using cross-validation by comparing, for each channel of the multi-channel sensor device, results of the first situation to results of the second situation in the time domain wherein, for each channel, the difference between the results of the first situation and the results of the second situation indicate the sensor noise and/or artifacts for that channel.

4. The system of any one of examples 1-3 wherein the computing device is configured to estimate the time-domain amplitude components using cross-validation by applying the spatial model with the channel under investigation excluded from the data and the spatial model, wherein the difference in the temporal domain between the decomposition and the original data for the channel under investigation indicates the sensor noise and/artifacts of the channel under investigation, and
   wherein the computing device is further configured to suppress the identified sensor noise and/or artifacts from the data by finding the temporal waveform common to the channel under investigation and the decomposition.

5. The system of any one of examples 1-4 wherein the data spans a first length of time, and wherein the computing device is further configured to:
   divide the data into a plurality of time segments that each span lengths of time shorter than the first length of time; and
   perform steps (b)-(f) separately for each time segment.

6. The system of example 5 wherein at least some of the time segments are overlapping in time.

7. A method, comprising:
   (a) receiving spatially oversampled multi-channel sensor data from a region of interest;
   (b) building a spatial model from the data for essential spatial degrees of freedom;
   (c) decomposing the data into the underlying spatial model to obtain associated amplitude components containing a mixture of original temporal waveforms of the data; and
   (d) for each channel of the multi-channel sensor, estimating time-domain amplitude components using cross-validation;

based on the estimated time-domain amplitude components, identifying sensor noise and/or artifacts for that channel; and suppressing the identified sensor noise and/or artifacts from the data.

8. The method of example 7 wherein decomposing the data into the underlying spatial model comprises decomposing the data in two situations for each channel of the multi-channel sensor device, the two situations including:

a first situation in which the amplitude components are estimated when applying the spatial model to all channels; and a second situation in which the amplitude components are estimated when applying the spatial model with the channel under investigation excluded from the data and the spatial model;

wherein estimating the time-domain amplitude components using cross-validation comprises comparing, for each channel of the multi-channel sensor device, results of the first situation to results of the second situation in the time domain wherein, for each channel, the difference between the results of the first situation and the results of the second situation indicate the sensor noise and/or artifacts for that channel.

9. The method of example 8 wherein comparing, for each channel of the multichannel device, results of the first situation to results of the second situation in the time domain comprises implementing an orthogonal projection operation.

10. The method of example 8 wherein comparing, for each channel of the multichannel device, results of the first situation to results of the second situation in the time domain comprises implementing a singular value decomposition of the temporal domain signals of the amplitude coefficients corresponding to the spatial model to find a temporal basis.

11. The method of any one of examples 7-10 wherein estimating the time-domain amplitude components using cross-validation comprises applying the spatial model with the channel under investigation excluded from the data and the spatial model, wherein the difference in the temporal domain between the decomposition and the original data for the channel under investigation indicates the sensor noise and/artifacts of the channel under investigation, and wherein suppressing the identified sensor noise and/or artifacts from the data comprises finding the temporal waveform common to the channel under investigation and the decomposition.

12. The method of example 11 wherein suppressing, for each channel of the multichannel device, the sensor noise and/or artifacts by finding the temporal waveform common to the channel under investigation and the decomposition comprises projecting the original channel waveform to a temporal basis spanned by the decomposed amplitude coefficients by a parallel projection operator.

13. The method of example 12 wherein projecting the original channel waveform to a temporal basis spanned by the decomposed amplitude coefficients by a parallel projection operator comprises implementing a singular value decomposition of the temporal domain signals of the amplitude coefficients corresponding to the spatial model to find the temporal basis.

14. The method of any one of examples 7-13 wherein suppressing, for each channel of the multichannel device, the sensor noise and/or artifacts from the signal of interest comprises implementing an orthogonal projection operator.

15. The method of any one of examples 7-14 wherein building the spatial model for the essential spatial degrees of freedom comprises implementing a combination of a basic solution of Laplace's equation for the harmonic scalar potential determining the magnetic field in the measurement area to calculate a spatial basis.

16. The method of any one of examples 7-15 wherein building the spatial model for the essential spatial degrees of freedom comprises using dominating spatial patterns found in a statistical analysis of the original data to calculate a spatial basis.

17. The method of example 16 wherein using dominating spatial patterns found in a statistical analysis of the original data to calculate a spatial basis comprises using dominating spatial patterns found in a principle component analysis.

18. The method of any one of examples 7-17 wherein the data spans a first length of time, the method further comprising:

dividing the data into a plurality of time segments that each span lengths of time shorter than the first length of time; and performing steps (b)-(d) separately for each time segment.

19. The method of example 18, wherein at least some of the time segments are overlapping in time.

20. A computer-readable medium storing instructions that, when executed by one or more processors, cause the processors to perform operations comprising:

(a) receiving spatially oversampled multi-channel sensor data from a region of interest;

(b) building a spatial model from the data for essential spatial degrees of freedom;

(c) decomposing the data into the underlying spatial model to obtain associated amplitude components containing a mixture of original temporal waveforms of the data;

(d) for each channel of the multi-channel sensor, estimating time-domain amplitude components using cross-validation;

(e) for each channel, based on the estimated time-domain amplitude components, identifying sensor noise and/or artifacts for that channel; and (f) for each channel, suppressing the identified sensor noise and/or artifacts from the data.

21. The computer-readable medium of example 20 wherein decomposing the data into the underlying spatial model comprises decomposing the data in two situations for each channel of the multi-channel sensor device, the two situations including:

a first situation in which the amplitude components are estimated when applying the spatial model to all channels; and a second situation where the amplitude components are estimated when applying the spatial model with the channel under investigation excluded from the data and the spatial model;

wherein estimating the time-domain amplitude components using cross-validation comprises comparing, for each channel of the multi-channel sensor device, results of the first situation to results of the second situation in the time domain wherein, for each channel, the difference between the results of the first situation and the results of the second situation indicate the sensor noise and/or artifacts for that channel.

22. The computer-readable medium of example 21 wherein comparing, for each channel of the multichannel device, results of the first situation to results of the second situation in the time domain comprises implementing an orthogonal projection operation.

23. The computer-readable medium of any one of examples 20-22 wherein estimating the time-domain amplitude components using cross-validation comprises applying the spatial model with the channel under investigation excluded from the data and the spatial model, wherein the difference in the temporal domain between the decomposition and the original data for the channel under investigation indicates the sensor noise and/artifacts of the channel under investigation, and wherein suppressing the identified sensor noise and/or artifacts from the data comprises finding the temporal waveform common to the channel under investigation and the decomposition.

24. The computer-readable medium of example 23 wherein suppressing, for each channel of the multichannel device, the sensor noise and/or artifacts by finding the temporal waveform common to the channel under investigation and the decomposition comprises projecting the original channel waveform to a temporal basis spanned by the decomposed amplitude coefficients by a parallel projection operator.

25. The computer-readable medium of any one of examples 20-24 wherein the data spans a first length of time, and wherein the operations further comprise:

dividing the data into a plurality of time segments that each span lengths of time shorter than the first length of time; and performing steps (b)-(f) separately for each time segment.

26. The computer-readable medium of example 25 wherein at least some of the plurality of segments are overlapping in time.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, in some embodiments, the technology can be used, for example, to reduce noise in data other than electrical or magnetic signals, for example economic or other data. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

APPENDIX A

Spatial Sensor Noise Suppression

Under the assumption of spatial oversampling, the contribution of $E_u$ can be suppressed by cross-validation. A spatial CV operator $K$ can be constructed to compute denoised data matrix $\tilde{D}$ as $$\tilde{D}=KD \tag{7}$$

In this CV formulation, $K$ is an N×N matrix with zeros on the diagonal. Because this operator reconstructs each channel $d_j$ using only a weighted combination of the other channels $d_{j'\neq j}$, it eliminates the contribution of individual noise of $d_j$ from the denoised $\tilde{d}_j$. Here, the d-vectors consist of the sampled signals corresponding to the channel under investigation and are thus $n_s$-dimensional.

However, this benefit comes at the expense of also contaminating $\tilde{d}_j$ with the sensor noise from $d_{j'\neq j}$. It is thus critical to minimize spreading of artifacts and noise through appropriate weights in the K matrix off-diagonals. Therefore, the theoretical effects of such operators on this data must be examined.

1) Operator properties: In principle, any N×N-dimensional matrix K with a zero diagonal could be a CV matrix, providing a cross-validated estimate of the data $$\tilde{D}=KD=(KM)X+KE_u \tag{8}$$

with $K(j, j)=0$ $\forall j$. Any such operator will minimize the diagonal elements of the initially diagonal noise covariance, as the covariance $C_u = E[E_u E_u^T]$ will be transformed to $$\tilde{C}_u = E[KE_u E_u^T K^T] = KC_u K^T. \tag{9}$$

It is not guaranteed, however, that any K would result in small off-diagonal elements in covariance $\tilde{C}_u$, which needs to be taken into account in the design of the operator K. The trivial example K=0 satisfies the condition K (j, j)=0 and minimizes the off-diagonal elements of $\tilde{C}_u$, but it would lead to KM=0, and, consequently, all signal of interest would be lost as well.

A good sensor noise suppression operator K should:
1) Minimize spatial bias of the signal of interest.
2) Minimize spatial spreading of channel artifacts.
3) Maximize the suppression of sensor noise (ratio of diagonal elements of $C_u$ and $\tilde{C}_u$).

Comparing eqs. 3 and 8, the requirement of no spatial bias becomes KMX=MX, or (K−I) M where I is the N×N identity matrix. For no spatial bias to occur, matrix K−I thus has to belong to the left null space of the data-dependent matrix MX, which is spanned by the rows of $U^T$ that correspond to zero-valued singular values of the SVD decomposition MX=UΣV$^T$. See Appendix A for a formulation based on this principle.

If one uses a matrix K that distorts the spatial profile of the signal of interest, then for many subsequent analyses this must be taken into account. For example, in MEG the aim is often to estimate the underlying neural current distribution y. The estimation process requires that the N-dimensional sensor-level signal distribution b produced by a set of $n_q$ neural current elements be calculated, each characterized with an N-dimensional lead field $l_k$. Given an $n_q$-dimensional amplitude distribution y, the model is b=Ly, where L=[$l_1, l_2, \ldots, l_{n_q}$] is the N×$n_q$-dimensional model matrix. By fitting this model to the acquired data, the amplitudes are estimated as $\hat{y}=L^\dagger D$, which is associated with a source-level noise covariance $$C_{uy} = L^\dagger \tilde{C}_u L^{\dagger T}. \tag{10}$$

In case of a non-biasing sensor noise suppression operator $K_M$, the source-space noise covariance is $$\tilde{C}_{uy} = L^\dagger \tilde{C}_u L^{\dagger T}. \quad (11)$$

Where $\tilde{C}_u = KMC_u K_M^T$, and the noise suppression performance is preserved in the source space. If spatial bias is expected, however, one has to compensate for the bias of K at the lead field level during localization to ensure that the model matches the data as $$KD = KLy. \quad (12)$$

This leads to $\hat{y} = (KL)^\dagger KD$, corresponding to source space noise covariance $$\begin{aligned}\tilde{C}_{uy} &= (KL)^\dagger \tilde{C}_u (KL)^{\dagger T} \quad (13)\\ &= (KL)^\dagger K C_u K^T (KL)^{\dagger T}\\ &= L^\dagger C_u L^{\dagger T}\\ &= C_{uy},\end{aligned}$$

where it is assumed that K and L are full-rank matrices ($(KL)^\dagger = L^\dagger K^\dagger$). Thus, the sensor noise suppression performance is lost in the source space in case lead field compensation is required.

In prior work, multiple potential formulations for spatial operators were provided, e.g., using a weighted average of sensors based on physical proximity. However, the most general formulation uses the temporal correlations between channels to construct $K_{SNS}$. Specifically, assuming that D has zero sample mean, to get the non-j coefficients $\kappa_j$ for row j of $K_{SNS}$ (where the subscript $\notin j$ indicate the exclusion of channel j):

1) Compute the PCA of $D_{\notin j}$ (eigenvalues $\lambda$ and eigenvectors A of the covariance matrix $C_{\notin j}$).
2) Compute weighted eigenvectors $A_w = \text{diag}(\sqrt{\lambda})A$ (where the square root is taken element-wise).
3) Project $j^{th}$ row (omitting column j) of the full covariance C onto this subspace to obtain $k_j = A_w c_j A_w$.

This formulation can be modified to use only a subset of channels $1 < N_{neighbors} < N$ by subselecting $N_{neighbors}$ rows and columns of C according to some criteria, e.g., the j:th row of the correlation matrix $C_N$, obtained by dividing the rows and columns of C by the square root of the diagonal elements of C.

APPENDIX B

Controlling Bias

In the spatial-domain formulation, properly controlling of the spatial bias requires access to MX. This is facilitated if the data-independent matrix M or any other matrix that spans the same signal subspace as M is known because then, under the assumption of spatial oversampling, eq. 2 indicates that cross-validation for any channel j can be expressed as $$\hat{d}_j^T = m_j^T M_{\notin j}^\dagger D_{\notin j} = d_0^T + m_j^T M_{-j}^\dagger E_{u, \notin j}, \quad (14)$$

where $m_j^T$ is the j:th row in matrix M, subscript $\notin j$ indicates exclusion of channel j, and $\dagger$ means pseudoinverse. Now, the j:th row of matrix K can be constructed by setting the values of the $1 \times (N-1)$-dimensional row vector $m_j^T M_{-j}^\dagger$ on off-diagonal entries of the j:th row of K. To emphasize that information about matrix M was used in the derivation of the CV matrix, the introduce subscript M is introduced as follows:

$$\hat{D} = K_M D = D_0 + K_M E_u \quad (15)$$

In this formulation, no spatial bias is introduced, as demonstrated by eq. 14, but the random noise contribution changes from $E_u$ to $K_M E_u$. Note that $K_M$ has zeros at least on the diagonal, so each channel's own noise contribution is completely eliminated from the channel itself.

According to eq. 9, the noise covariance is now $$\tilde{C}_{u,M} = E[K_M E_u E_u^T K] = K_M C K_M^T. \quad (16)$$

It is to be noted that in such a purely spatially driven sensor noise suppression method, the inter-channel artifact spreading, manifested by non-zero off diagonal elements in $\tilde{C}_{u,M}$ depends on the physical and geometrical condition of the measurement arrangement. For example, in MEG the $K_M$ would change with changing position of the subject's head with respect to the sensors, leading to sensor noise suppression performance dependent on the head position.

APPENDIX C

Temporal Orthogonality and Spatial Rank-Reduction

The temporal information is preserved in the estimate of the model parameters:

$$\hat{X} = M^\dagger D = X + M^\dagger E_u, \quad (17)$$

where the last term $M^\dagger E_u$ represents the projections of the $1 \times n_s$-dimensional random noise vectors of different channels onto an n-dimensional subspace. Now, let us consider a pair of random vectors $v_1$ and $v_2$ with elements that are statistically independent between the two vectors. Statistical independence means that at the statistical limit information about vector $v_1$ will not yield any information that could be used to infer properties of vector $v_2$, and vice versa. Therefore, not only the amplitude but also direction of these two vectors are uncorrelated at the statistical limit. That is, the larger the number of elements $n_s$ is in the two vectors, the closer the vectors are to orthogonality, and so:

$$\lim_{n_s \to \infty}(v_1 v_2^T) = 0. \quad (18)$$

Thus, assuming a large number of samples, for individual noise vectors corresponding to channels j and k, $\in_{uj} \in_{uk}^T = 0$ and therefore $\in_{uj} E_{u,\notin j}^T = 0$. Here the j:th row of $E_u$ is denoted as $\in_j$. Comparing this with the projected space yields $M_{\notin j}^\dagger E_{u,\notin j} \in_{uk}^T = 0$, which means that the original noise contribution of channel j is orthogonal to the noise contributions of other channels also in the projected space. Cross validation can be performed in the temporal space by estimating the waveforms from N−1 channels:

$$\hat{X}_{\notin j} = M_{\notin j}^\dagger D_{\notin j} = X + M_{\notin j}^\dagger E_{\notin j}, \quad (19)$$

assuming spatial oversampling. By performing a temporal domain analysis on $\hat{X}_{\notin j}$ that emphasizes the common waveforms, rows of X, one can find an $n_s \times n_t$-dimensional ($n_t \leq n$) orthonormal temporal subspace $V_{\notin j}$ that spans X but has no contribution of $\in_{uj}$. Then $$\hat{d}_j = d_j V_{\notin j} V_{\notin j}^T = (d_{0j} + \in_{uj}) V_{\notin j} V_{\notin j}^T, \quad (20)$$

where $\in_{uj}V_{\notin j}V_{\notin j}^T$ represents the parallel projection of the individual noise vector of channel j onto the temporal subspace derived from all other channels. With large $n_s$, the subspace $V_{\notin j}V_{\notin j}^T$ and vector $E_j$ are very close to orthogonality due to statistical independence and therefore $\in_{uj}V_{\notin j}V_{\notin j}^T \approx 0$. On the other hand, by determining the temporal subspace $V_{\notin j}$ in a way that emphasizes the common waveforms, X, over the random vectors in $E_{u,\notin j}$, the angle between $d_{0j}=m_jX$ and V is small. Thus, $d_{0j}V_{\notin j}V_{\notin j}^T \approx d_{0j}$ and eq. 20 becomes $$d_j \approx d_{0j}. \quad (21)$$

If the statistical assumptions hold true, the temporal cross-validation method introduces minimal spatial bias and maximal sensor noise suppression performance. Thus, the techniques disclosed herein do away with the inherent problems of spatial bias and inter-channel artifact spreading of the spatial models. Now the limitations are posed by statistical properties of the data rather than inherent complications of spatial-domain operations.

We claim:

1. A multi-channel sensor system, comprising:
   a multi-channel sensor configured to obtain spatially oversampled data; and
   a computing device communicatively coupled to the multi-channel sensor, the computing device configured to—
   (a) receive the spatially oversampled data from the multi-channel sensor;
   (b) build a spatial model from the data for essential spatial degrees of freedom;
   (c) decompose the data into the underlying spatial model to obtain associated amplitude components containing a mixture of original temporal waveforms of the data;
   (d) for each channel of the multi-channel sensor, estimate time-domain amplitude components using cross-validation;
   (e) for each channel, based on the estimated time-domain amplitude components, identify sensor noise and/or artifacts for that channel; and
   (f) for each channel, suppress the identified sensor noise and/or artifacts from the data,
   wherein the computing device is configured to estimate the time-domain amplitude components using a cross-validation by applying the spatial model with the channel under investigation excluded from the data and the spatial model, wherein the difference in the temporal domain between the decomposition and the original data for the channel under investigation indicates the sensor noise and/or artifacts of the channel under investigation, and
   wherein the computing device is further configured to suppress the identified sensor noise and/or artifacts from the data by finding the temporal waveform common to the channel under investigation and the decomposition.

2. The system of claim 1 wherein the multi-channel sensor comprises at least one of: a magnetoencephalographic (MEG) sensor array or an electroencephalographic (EEG) sensor array.

3. The system of claim 1 wherein the computing device is configured to decompose the data into the underlying spatial model by decomposing the data in two situations for each channel of the multi-channel sensor device, the two situations including:
   a first situation in which the amplitude components are estimated when applying the spatial model to all channels; and
   a second situation in which the amplitude components are estimated when applying the spatial model with the channel under investigation excluded from the data and the spatial model; and
   wherein the computing device is further configured to estimate the time-domain amplitude components using cross-validation by comparing, for each channel of the multi-channel sensor device, results of the first situation to results of the second situation in the time domain wherein, for each channel, the difference between the results of the first situation and the results of the second situation indicate the sensor noise and/or artifacts for that channel.

4. The system of claim 1 wherein the data spans a first length of time, and wherein the computing device is further configured to:
   divide the data into a plurality of time segments that each span lengths of time shorter than the first length of time; and
   perform steps (b)-(f) separately for each time segment.

5. The system of claim 4, wherein at least some of the time segments are overlapping in time.

* * * * *